United States Patent [19]

Rainin et al.

[11] Patent Number: 4,577,760
[45] Date of Patent: Mar. 25, 1986

[54] APPARATUS FOR SUPPORTING PIPETTE TIPS

[75] Inventors: Kenneth Rainin, Piedmont; Stephen Ruskewicz, Kensington, both of Calif.

[73] Assignee: Rainin Instrument Company, Inc., Emeryville, Calif.

[21] Appl. No.: 650,505

[22] Filed: Sep. 14, 1984

[51] Int. Cl.⁴ .............................................. B65D 85/30
[52] U.S. Cl. .................... 206/508; 206/486; 220/366
[58] Field of Search ............... 206/508, 436, 443, 486, 206/562, 569, 571; 220/203, 202, 366, 367

[56] References Cited

U.S. PATENT DOCUMENTS

| | | | |
|---|---|---|---|
| D. 271,239 | 11/1983 | Lemieux et al. | D24/02 |
| 3,082,904 | 3/1963 | Newcomb et al. | 220/203 |
| 3,381,872 | 5/1968 | Holder et al. | 220/366 X |
| 3,494,201 | 2/1970 | Roach | 73/425.6 |
| 3,853,217 | 12/1974 | Scordato et al. | 206/486 X |
| 3,937,322 | 2/1976 | Cohen | 206/216 |
| 4,234,100 | 11/1980 | Chabot | 220/366 X |
| 4,235,338 | 11/1980 | Dugan et al. | 206/508 X |
| 4,256,240 | 3/1981 | Woinarski | 206/508 X |
| 4,349,109 | 9/1982 | Scordato et al. | 206/486 X |
| 4,358,908 | 11/1982 | Song | 220/366 X |
| 4,399,159 | 8/1983 | Guibert | 220/366 X |

FOREIGN PATENT DOCUMENTS 1475924  2/1967  France .

Primary Examiner—Steven M. Pollard
Attorney, Agent, or Firm—Bielen & Peterson

[57] ABSTRACT

An enclosed pipette tip rack utilizing a container having a bottom and a side portion connected to the bottom which extends upwardly and terminates in a top. A tray is supported by the container and holds at least one pipette tip such that a portion of the pipette tip lies within the container. A cover is also included and is supported by the container adjacent the tray. The container and cover are vented to the ambient environment.

14 Claims, 16 Drawing Figures

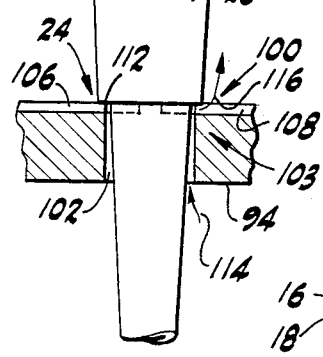
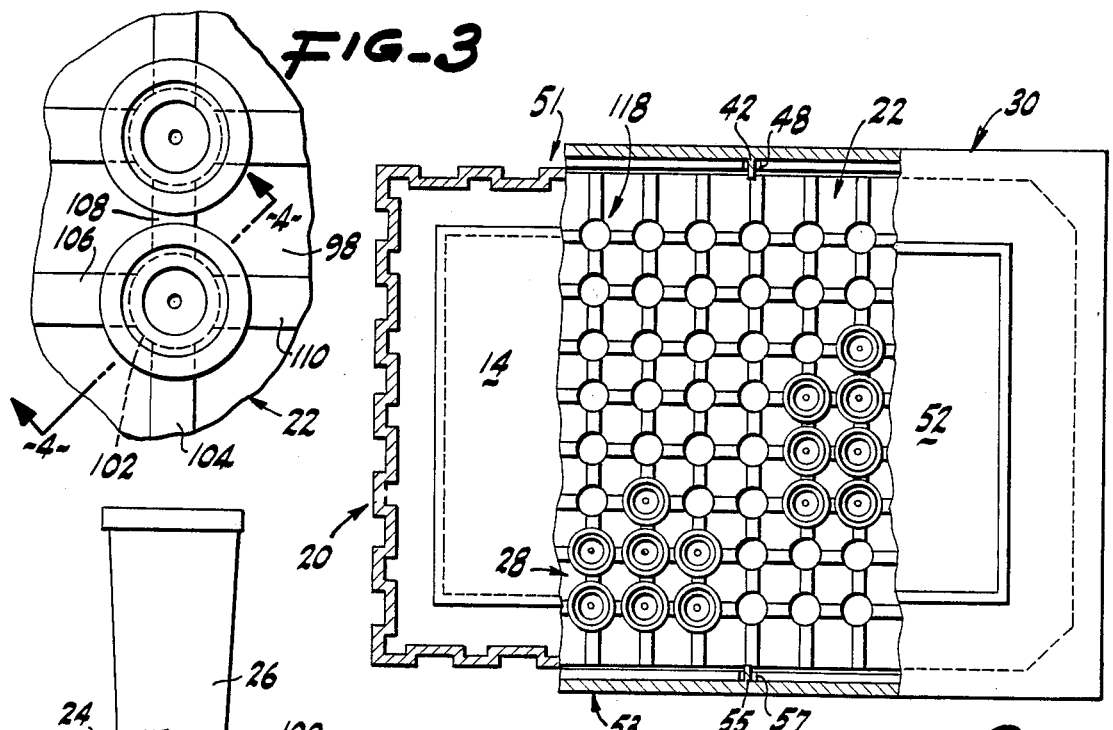
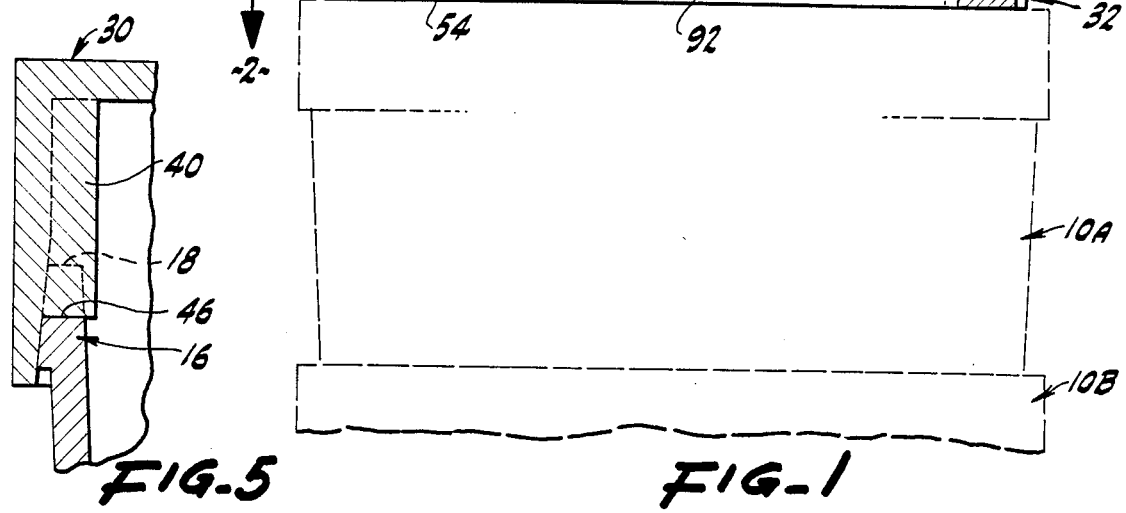

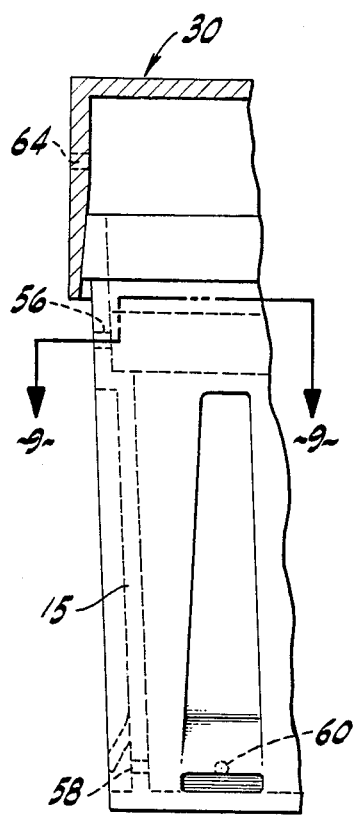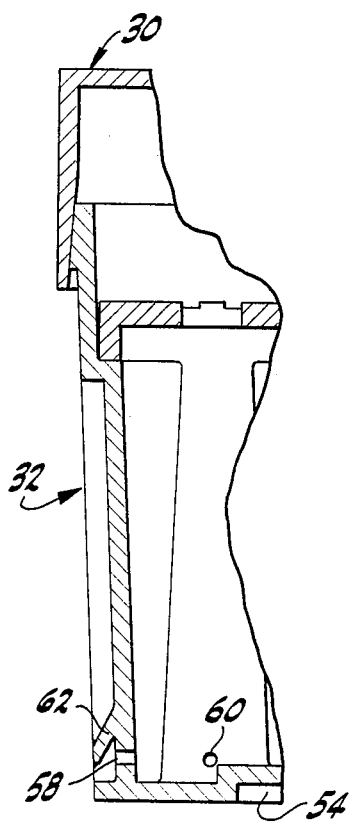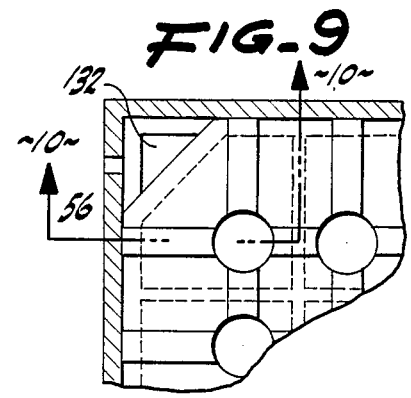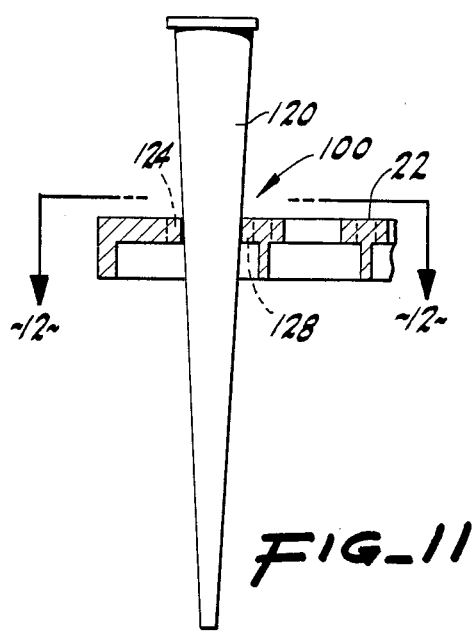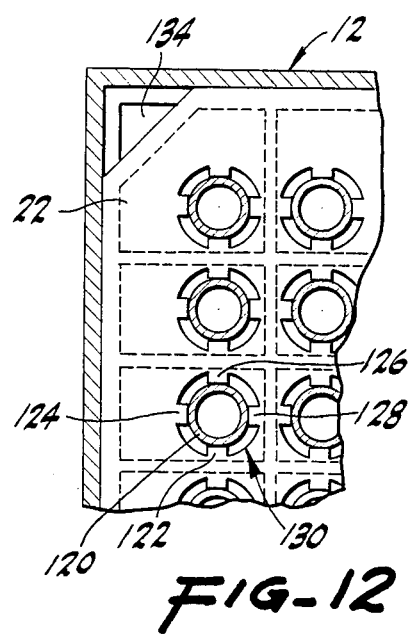

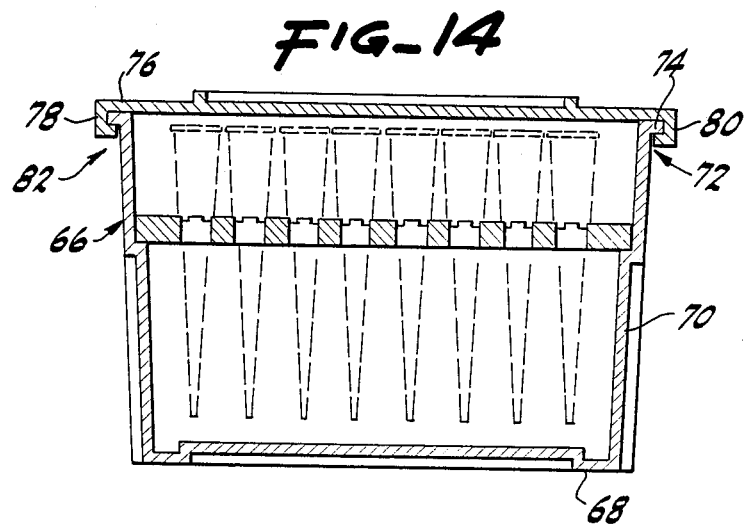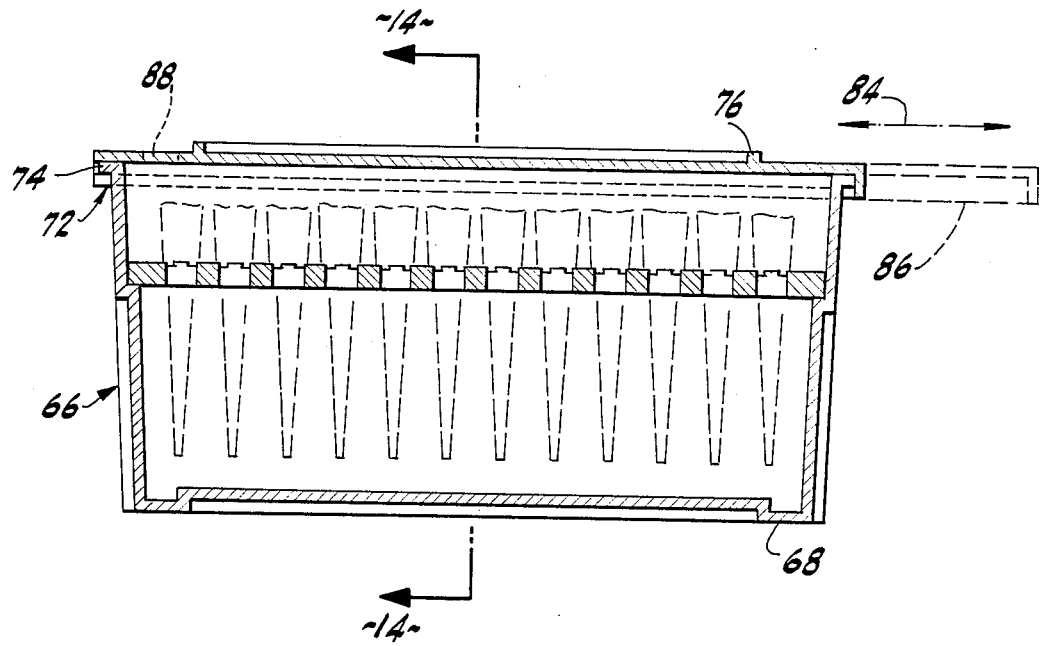

APPARATUS FOR SUPPORTING PIPETTE TIPS

BACKGROUND OF THE INVENTION

In accordance with the present invention a novel enclosed pipette tip rack is provided.

Disposable pipette tips have often been packaged in supporting trays. Such disposable pipette tip trays function to organize and to aid the user of the same in the placement of the disposable pipette tip on a pipette. Prior pipette tip trays generally had an open bottom and top. For example U.S. Pat. No. 3,494,201 describes a tray or rack for disposable pipette tips and the system for use of the same.

Packages have also been devised to ship and store stackable pipette tip racks. Such packages are also intended to protect the disposable pipette tips held therewithin from any type of contamination or physical damage. For example reference is made to U.S. Pat. No. 3,853,217, to Scordato, U.S. Pat. No. 3,937,322 to Cohen and French Pat. No. 1,475,924, in this regard.

Design Pat. No. D. 271,239 issued to Lemieux et al describes an individual container and rack for pipette tips which does not include the provision for nesting a plurality of the same as is depicted in the prior art, e.g. in U.S. Pat. No. 3,853,271 to Scorado et al. Moreover, the container and rack for pipette tips shown in U.S. Design Pat. No. D. 271,239 serves as a unitary package for disposable pipette tips and maybe autoclaved. During autoclaving the top of the container and rack may be tilted to allow circulation of ambient gases to the interior of the container as shown in a brochure issued by the assignee of U.S. Design Pat. No. D. 271,239. Open racks of the prior art are often autoclaved in cardboard boxes or metal foil containers hand fashioned for that purpose.

These prior disposable pipette tips racks and containers and the techniques employed for autoclaving the same involve undesirable aspects. For example, the method of tilting the cover on the container and rack shown in U.S. Design Pat. No. D. 271,239 is unreliable since the top is difficult to balance in a tilted position and may shift from that position during an autoclaving process. In addition, the top must be repositioned after the autoclaving process to prevent contimation from dust, moisture, and other airborne contaminants. Using a secondary container for the autoclaving is cumbersome, expensive, and often results in contamination of the disposable pipette tip in the rack during the autoclaving process.

A disposable enclosed pipette tip rack which solves the problems encountered in the prior art, especially during the autoclaving process, would be a great advance in the scientific and medical field.

SUMMARY OF THE INVENTION

In accordance with the present invention a novel and useful enclosed pipette tip rack is provided.

The enclosed pipette tip rack of the present invention utilizes a container which has a bottom and a side portion connected to the bottom. The side portion extends outwardly and upwardly from the bottom to form a top. Such a top may take the form of an edge portion. A tray capable of holding at least one pipette tip is supported within the container. Also, a cover is provided which is supported by the container or which is indirectly supported by the tray. The cover and container form an enclosure for the pipette tips being held by the tray.

The pipette tip rack may also be defined to include means for venting the enclosure. Such means for venting the enclosure may take the form of means for separating the cover from the top portion which may be in the form of an edge. Thus, a gap may be formed between the cover and the side portion of the enclosure. Such means for separating the cover from the top portion of the enclosure may include at least one element connected to the cover such that the container side portion would bear on the same to form the ventilation gap between the top portion and the cover of the enclosure. Likewise, at least one element may be connected to the container such that the cover bears on or rests on the same to form the heretofore described ventilation gap. In one embodiment, the container and cover may each include an element. In such a case the cover may be positioned on the container in a first position such that the cover element is supported by the container element forming a gap between the top portion of the container and the cover. Also, the cover is capable of being positioned in a second position such that the cover engages the top portion of the container and the cover element is free of support from the element of side portion. In this configuration the gap between the top of the container and the cover will be eliminated and the enclosure would be a configuration for resisting dust intrusion.

The pipette tip rack of the present invention may also be constructed with means for sliding the cover in relation to the top portion of the container. Consequently, the means for sliding the cover may also serve as means for separating the cover from the top portion of the container to effect ventilation of the enclosure.

The enclosure formed by the container and the cover heretofore described, may also be vented by simply forming an opening through the enclosure itself. This may entail an opening being formed in the cover and/or the container of the enclosure formed thereby. A roof or overhang may be constructed to extend from the exterior of the enclosure adjacent the opening through the same.

The tray supported by the container within the enclosure is positioned to form a first chamber between one side of the tray and the container bottom. In addition, a second chamber is formed between another side of the tray container top. The first and second chambers communicate with one another by means for joining the same together. The pipette tip, and in most cases a plurality of pipette tipe are held to the tray by an opening or openings through the same. A shoulder is formed on the another side of the tray to engage any pipette tip being held in the opening to the tray. The shoulder forms a space between the exterior of the pipette tip and the portion of the tray surrounded by the opening therethrough. The shoulder may extend into the second chamber in this configuration. Similarly, a protuberance may be formed from the portion of the tray surrounding the opening through the tray. Such a protuberance may be set to lie between the first and second chambers and to contact the exterior of the pipette tip being held in the opening through the tray. Thus, a space would also be formed between the exterior of the pipette tip and the rim of the opening in either configuration. Fluids such as air may flow between the first and second chambers formed by the tray within the container. Moreover, an opening may be formed through the tray apart from the openings employed to hold pipette tips.

It may be apparent that a novel and useful pipette tip rack has been described.

It is therefore an object of the present invention to provide a pipette tip rack which is fully autoclavable and permits the autoclaving gas to freely contact the pipette tips within the enclosed rack.

It is another object of the present invention to provide a pipette tip rack which is capable of being placed in an autoclavable mode or a dust free mode depending on the position of the cover enclosing the rack.

It is yet another object of the present invention to provide a pipette tip rack which permits free communication between first and second chambers formed by a tray which holds the disposable pipette tips within the enclosed rack.

Another object of the present invention is to provide a pipette tip rack for holding disposable pipette tips which includes a cover which is removable and replaceable using only one hand of the person employing the pipette tip rack.

Another object of the present invention is to provide a pipette tip rack which may be steam autoclaved and which minimizes the condensation of steam in the vicinity of the disposable tips.

A further object of the present invention is to provide a pipette tip rack which requires a minimum of handling and therefore reduces the possibility of contamination of the pipette tips within the pipette tip rack.

The invention possesses other objects and advantages especially as concerns particular characteristics and features thereof which will become apparent as the specification continues.

BRIEF DESCRIPTION OF THE DRAWINGS

FIG. 1 is a sectional view of the pipette tip rack of the present invention showing a second rack in phantom to illustrate the stacking feature thereof.

FIG. 2 is a sectional view taken along line 2—2 of FIG. 1.

FIG. 3 is an enlarged top plan view of a pair of openings occupied by pipette tips of the tray portion of the pipette tip rack depicted in FIG. 2.

FIG. 4 is a sectional view taken along line 4—4 of FIG. 3 showing a broken side view of a pipette tip.

FIG. 5 is an enlarged partial sectional view showing the detail of the upper edge portion of the rack depicted in FIG. 1 along line 5—5 thereof.

FIG. 8 is a partial sectional view showing an alternate embodiment of the ventilation means of the rack of the present invention.

FIG. 9 is a view taken along line 9—9 of FIG. 8 depicting the ventilation means between the first and second chambers of the rack of the present invention.

FIG. 10 is a sectional view of rack of the present invention showing an alternate embodiment of the ventilation means therein.

FIG. 11 is a sectional view depicting ventilation means between the first and second chambers of the pipette tip rack using a pipette tip having a purely conical shape.

FIG. 12 is a view taken along 12—12 of FIG. 11.

FIG. 13 is a vertical sectional view of an alternate embodiment of the pipette tip rack of the present invention having a sliding cover.

FIG. 14 is a view taken along line 14—14 of FIG. 13.

Figure 6:
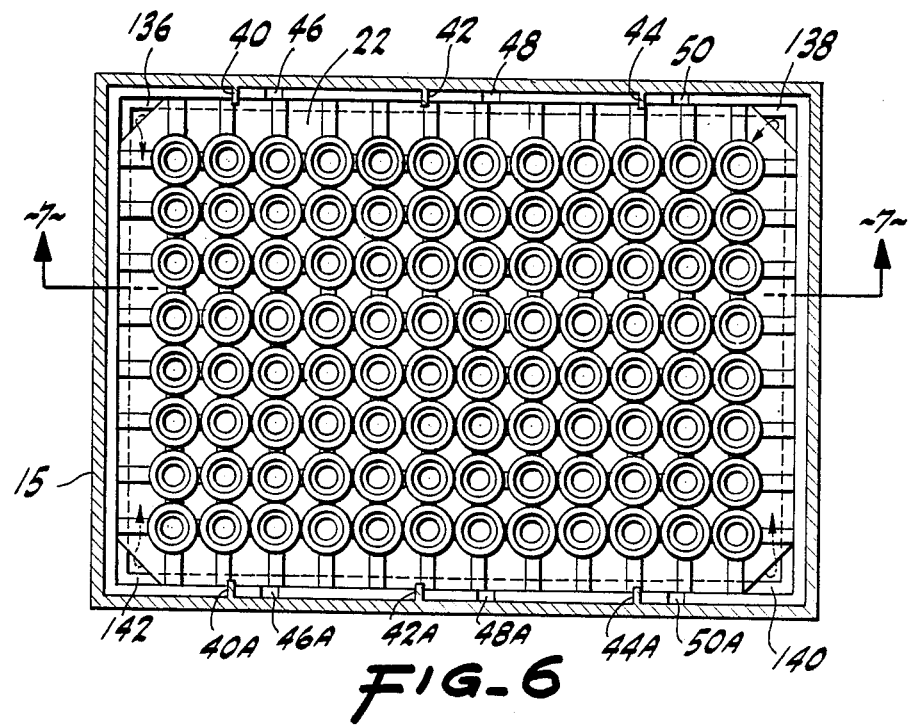
FIG. 6 is a horizontal sectional view of the pipette tip rack shown in FIG. 1 emphasizing the tray portion within the rack.

For a better understanding of the invention reference is made to the following detailed description of the preferred embodiments thereof which will be disclosed hereinafter.

DESCRIPTION OF THE PREFERRED EMBODIMENTS

Various aspects of the present invention will evolve from the following detailed description of the preferred embodiments thereof which should be referenced to the hereinabove described drawings.

The invention as a whole is shown on the drawings by reference character 10. The pipette tip rack 10 includes as one of its elements a container 12, FIG. 1. Container 12 is constructed with a bottom 14 and a side portion 15 which, in the embodiment shown in FIG. 1 is continuous with bottom 14 and extends upwardly therefrom. Side portion 14 terminates in a top portion 16 having a top surface 18 which extends completely around container 12. Although container 12 may take any shape, in the embodiments shown in FIGS. 1 and 2, container 12 takes a rectangular solid configuration having a slightly tapered side portion 15. Side portion 15 may include a series of projections and recesses forming a generally fluted facade 20, FIG. 2 which strengthens container 12 and confers asthetics qualities thereto.

The pipette tip rack 10 also is defined to possess a tray 22, FIGS. 1 and 2, which includes means 22 for holding at least one pipette tip 26 to tray 22. By way of illustration FIG. 1 depicts a plurality of pipette tips 28 which are partially within container 12.

Rack 10 also possesses as one of its elements a cover 30 which is supported by container 12 above and adjacent to tray 22. Cover 30 and container form an enclosure 32, FIG. 1, which encases plurality of pipette tips 28 held to rack 22. Plurality of pipette tips 28 do not touch bottom 14 or cover 30 within enclosure 32. Container 12 and cover 30 forming enclosure 32 may be constructed of a rigid or semi-rigid material. However, plastic material such as polyproplene is preferred since it has been found that this material easily withstands a typical sterilization temperature of 132° C. and a sterilization pressure of 1.9 kilograms per square centimeter. Also, polyproplene is resistant to chemical attack by sterilization gases such as steam, air, and ethylene oxide employed in autoclaving or sterilization processes.

Figure 7:
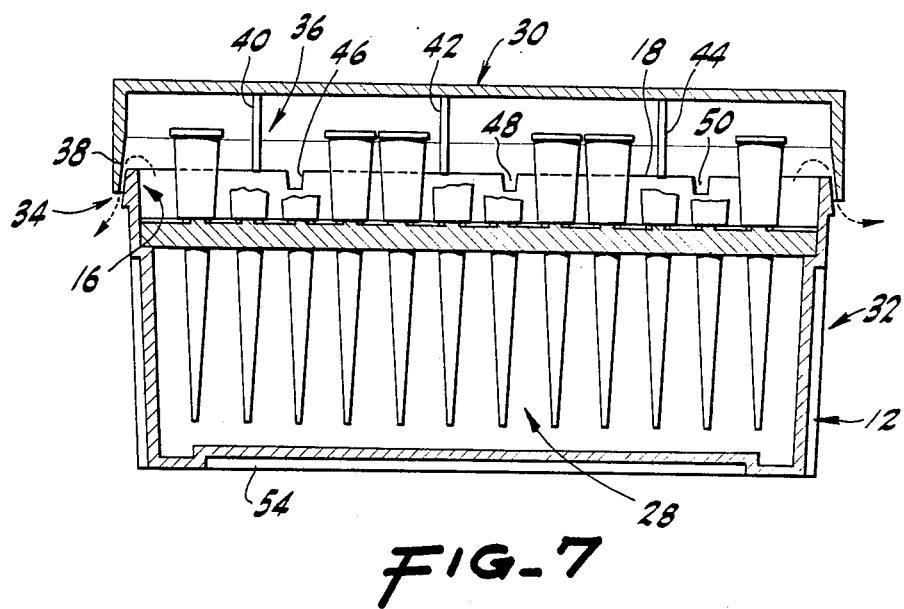
FIG. 7 is a view taken along line 7—7 of FIG. 6 showing the rack of the present invention in the autoclavable mode.

Enclosure 32 includes means 34 for venting the same, FIGS. 1 and 7. Means 34 is depicted in FIG. 7 as including means 36 for separating cover 30 from top portion 16 of container 12. A gap 38 forms between cover 30 and top portion 16 when rib elements 40, 42, and 44 rest on top surface 18, FIG. 7. When cover 30 is positioned in this first position shown in FIG. 7, enclosure 32 includes means 34 for venting enclosure 32. On the other hand, cover 30 may be turned approximately 180° and assume the configuration shown in FIG. 1 where ribs 40, 42, and 44 fit within recesses 46, 48 and 50 along sides of top portion 16 and similar ribs and recess along side portion 53 of top portion 16 (only rib 55 and recess 57 shown on FIG. 2). It should be apparent, that gap 38 does not form in this second position of cover 30 relative to container 12. Absent gap 38, enclosed rack 10 quite adequately resists the intrusion of dust and other contaminants to the interior of enclosure 32. This "dust-free" configuration is preferred for shipping and storing of pipette tip rack 10. In this aspect, cover 30 includes a raised portion 52 which fits into a recess 54 in bottom 14. Thus, containers 10, 10A and 10B, FIG. 1 may be stacked and partially nested during shipment.

Means 34 for venting enclosure 32 may also externalize in placing an opening through enclosure 32 such as openings 56, 58 and 60. Opening 58 may include a roof or awning-like structure 62 to control the intrusion of dust to the interior of enclosure 32. Means 34 for venting enclosure 32 may also include an opening 64 through cover 30, FIG. 8.

Means 34 for venting enclosure 32 and means 36 for separating cover 30 from container may also be defined as the embodiment shown in FIGS. 13 and 14. A container 66 includes a bottom portion 68 and side portion 70 extending upwardly therefrom. Side portion 70 includes a top portion having a flange 74. Cover 76 includes a pair of tracks 78 and 80 comprise means 82 for sliding cover 76 in relation to top portion 72 of container 66. FIG. 13 includes directional arrows 84 and a phantom portion 86 depicting the sliding cover 76. A gap 88 is formed between top portion 72 of side portion 70 and cover 76.

Returning to FIG. 1 it may be seen that tray 22 is supported by container 12 on a shoulder 90 which extends around the interior of enclosed pipette tip rack 10. Shoulder 90 is located at a height above bottom 14 such that plurality of pipette tips 28 do not touch the cover 30 or bottom 14 of enclosure 32. Tray 22 forms a first chamber 92 between side 94 of tray 98 and bottom 14 and a second chamber 96 between side 98 of tray 22 and cover 30. Means 100 is also provided for joining or connecting first chamber 92 to second chamber 96. With reference to FIGS. 3 and 4, it may be seen that means 24 for holding pipette tip 26 to tray 22 includes an opening 102 through tray 22. Shoulders or plateaus 104, 106, 108 and 110 extend upwardly from the side 98 of tray 22 and engage annulus 112 of pipette tip 126. Consequently a multiplicity of fluid passages 103 are formed between adjacent shoulders 104, 106, 108, 110 permitting communication between first and second chambers 92 and 96 per directional arrows 114 and 116, FIG. 4. As depicted in FIG. 2, tray 22 includes a plurality of openings 118 therethrough each capable of holding one of the plurality of pipette tips 28. A quarter of shoulders or plateaus is associated with each of the plurality of openings 118 to support each of the plurality of pipette tips 28 exmplified by pipette tip 26 in FIGS. 3 and 4.

FIGS. 11 and 12 illustrate an alternate embodiment of chamber connecting means 100 used in conjunction with a pipette tip 120 which does not include a shoulder. Protuberances 122, 124, 126 and 128 extend from tray 22 to contact the exterior of pipette tip 120. Thus, a plurality of passages 130 are formed between successive protuberances 124, 126 and 128 permitting fluids to pass from first chamber 92 to second chamber 96. In addition, chamber 92 and 96 may be connected by vents 132 and 134 formed by mitering corners of tray 22, FIGS. 9 and 12. FIG. 6 depicts tray 22 having each corner mitered forming vents 136, 138, 140 and 142.

Figure 15:
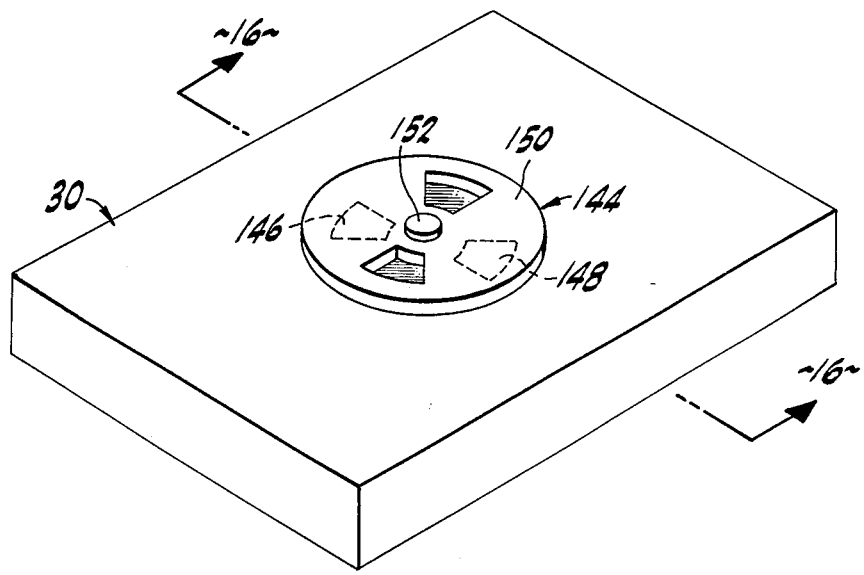
FIG. 15 is a perspective view of another embodiment of the present invention.
Figure 16:
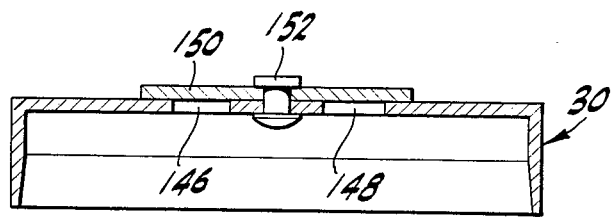
FIG. 16 is a view taken along line 16—16 of FIG. 15.

Means 34 for venting enclosure 32 may take the form illustrated in FIGS. 15 and 16 where a valve 144 is shown. Valve 144 is placed in cover 30 where a pair of openings 146 and 148 are shown. A disc 150 rotates on pin 152 which holds disc to cover 30. Thus, disc 150 may be rotated to open or close openings 146 and 148 (shown closed in FIG. 15.)

In operation, the user would load plurality of pipette tips 28 into plurality of openings 118 of tray 22. Tray 22 would be placed within container 12 and cover 30 would be positioned on top of container 22 in either the "dust-free" position, FIG. 1, or the autoclaving position, FIGS. 6 and 7. In the latter position the pipette tip rack 10 is placed in a sterilizing or autoclaving environment and fluids are free to enter and exit pipette tip rack 10 through venting means 34. In addition, between one another via means 100 which may include passages adjacent each pipette tip of the plurality of the pipette tip 28 or via the openings such as vents 136, 138, 140, and 142, FIG. 6. After autoclaving, the cover 30 may be placed in the "dust-free" position to maintain the sterility of the plurality of the pipette tip 28 within the pipette tip rack 10.

Tray 22 may be removed from enclosure 32 after plurality of pipette tips 28 are no longer usable. At this junction, cover 30 and enclosure 32 may form a case for any desired use.

While in the foregoing embodiments of the present invention have been set forth in the considerable detail for the purposes of making a complete disclosure of the invention, it may be apparent to those of skill in the art that numerous changes may be made in such detail without departing from the spirit and principles of the invention.

What is claimed is:

1. An apparatus for supporting pipette tips prising:
   a. a container having a bottom and a side portion connected to and extending from said bottom terminating in a top portion;
   b. a sole tray including means for holding at least one pipette tip thereto, said container further including means for supporting said tray such that at least a portion of the at least one pipette tip lies within said container;
   c. a cover, said cover being supported by said container adjacent said tray, said cover and container forming an enclosure for the at least one pipette tip, said tray forming a first chamber between one side thereof and said container bottom, and a second chamber between another side of said tray and said cover, said bottom of said container being capable of contacting said cover; and
   d. means for venting said enclosure, said venting means including means for separating and fixing said cover from said top portion of said side portion of said container, forming a gap therebetween, said venting means further including means for joining said first chamber to said second chamber to permit circulation of of fluid between said first and second chambers other than through any pipette top or means for holding any pipette tip to said sole tray and to permit circulation between the inside and outside of said enclosure.

2. The apparatus for supporting pipette tips of claim 1 in which said means for separating and fixing said cover from said top portion of said side portion includes at least one element connected to said cover, said cover element bearing on said side portion and forming said gap between said top portion of said side portion and said cover, thereby.

3. The apparatus for supporting pipette tips of claim 2 in which said container top portion includes a surface and said cover is capable of being positioned on said container in a first position in which said cover element is supported by said container top portion surface forming said gap between said top portion of said side portion and said cover, thereby, and said cover is capable of being positioned on said container in a second position such that said cover engages said top portion of said side portion and said element of said cover is free of support by said container top portion surface substantially eliminating said gap between said top portion of said side portion ans said cover, thereby.

4. The apparatus for supporting pipette tips of claim 1 in which said means for separating and fixing said cover from said top portion of said side portion includes at least one element connected to said container, said container element bearing on said cover and forming said gap between said top portion of said side portion and said cover, thereby.

5. The apparatus for supporting pipette tips of claim 1 which includes means for sliding said cover in relation to said top portion of said side portions, said means for sliding said cover also comprising said means for separating said cover from said top portion of said side portions.

6. The apparatus for supporting pipette tips of claim 1 in which said means for venting said enclosure includes an opening through said container.

7. The apparatus for supporting pippette tips of claim 1 in which said means for venting said enclosure includes an opening through said cover.

8. The apparatus for supporting pipette tips of claim 7 in which said means for venting said enclosure further comprises a roof extending from the exterior of said container adjacent said opening through said container.

9. The apparatus for supporting pipette tips of claim 1 in which said means for holding the at least one pipette tip comprises an opening through said tray and said means for joining said first and second chambers includes a shoulder connected to said another side of said tray, said shoulder engaging the at least one pipette tip to form a space between the exterior of the at least one pipette tip and the portion of the tray surrounding said opening through said tray.

10. The apparatus for supporting pipette tips of claim 1 in which said means for holding the at least one pipette tip comprises an opening through said tray, said opening including a surrounding portion formed by said tray between said first and second chambers of said container, and said means for joining said first chamber with said second chamber includes a protuberance on said portion of said tray surrounding said opening therethrough, said protuberance contacting the exterior of the at least one pipette tip to form a space between the exterior of the at least one pipette tip and the portion of the tray surrounding said opening through said tray.

11. The apparatus for supporting pipette tips of claims 1, 9, or 10 in which said means for joining said first and second chambers includes an opening through said tray.

12. The apparatus for supporting pipette tips of claim 1 in which said cover includes a boss and said top portion of said container includes a depression which is sized to fit said cover boss.

13. The apparatus for supporting pipette tips of claim 1 in which said tray is removable from said container.

14. The apparatus for supporting pipette tips of claim 1 in which said means for venting said enclosure includes a valve in said cover.

* * * * *